United States Patent [19]

Wurtman

[11] 4,435,424

[45] Mar. 6, 1984

[54] PROCESS FOR IMPROVING VIGOR AND MOOD IN NORMAL HUMAN PATIENTS

[75] Inventor: Richard J. Wurtman, Boston, Mass.

[73] Assignee: Massachusetts Institute of Technology, Cambridge, Mass.

[21] Appl. No.: 297,623

[22] Filed: Aug. 31, 1981

Related U.S. Application Data

[63] Continuation of Ser. No. 169,001, Jul. 15, 1980, abandoned, which is a continuation of Ser. No. 66,158, Aug. 13, 1979, abandoned, which is a continuation-in-part of Ser. No. 898,740, Apr. 24, 1978, abandoned.

[51] Int. Cl.$^3$ .......................................... A61K 31/195
[52] U.S. Cl. .................................................. 424/319
[58] Field of Search ........................................ 424/319

[56] References Cited
PUBLICATIONS

Wurtman et al., Science, 185–pp. 183–184, 7-12-74.
Gibson et al., Biochem. Pharmacology, 26, pp. 1137–1142, 6/77.
Chem. Abst., 79-87422S (1973).
Page, Scientific American, Dec. 1957, pp. 52–56.

Primary Examiner—Stanley J. Friedman
Attorney, Agent, or Firm—Arthur A. Smith, Jr.; Paul J. Cook

[57] ABSTRACT

The level of a catecholamine in neuronal synapses is increased in order to improve vigor by administering a neutral amino acid composition to a human wherein an increased brain level of a catecholamine is effected when the composition contains increased amounts of tyrosine and/or phenylalanine. Increased or decreased brain levels of serotonin are obtained when the amino acid composition contains increased or decreased amounts of tryptophan.

The neutral amino acid composition can be administered alone or concomitantly with a drug which increases or decreases catecholaminergic neurotransmission.

1 Claim, 1 Drawing Figure

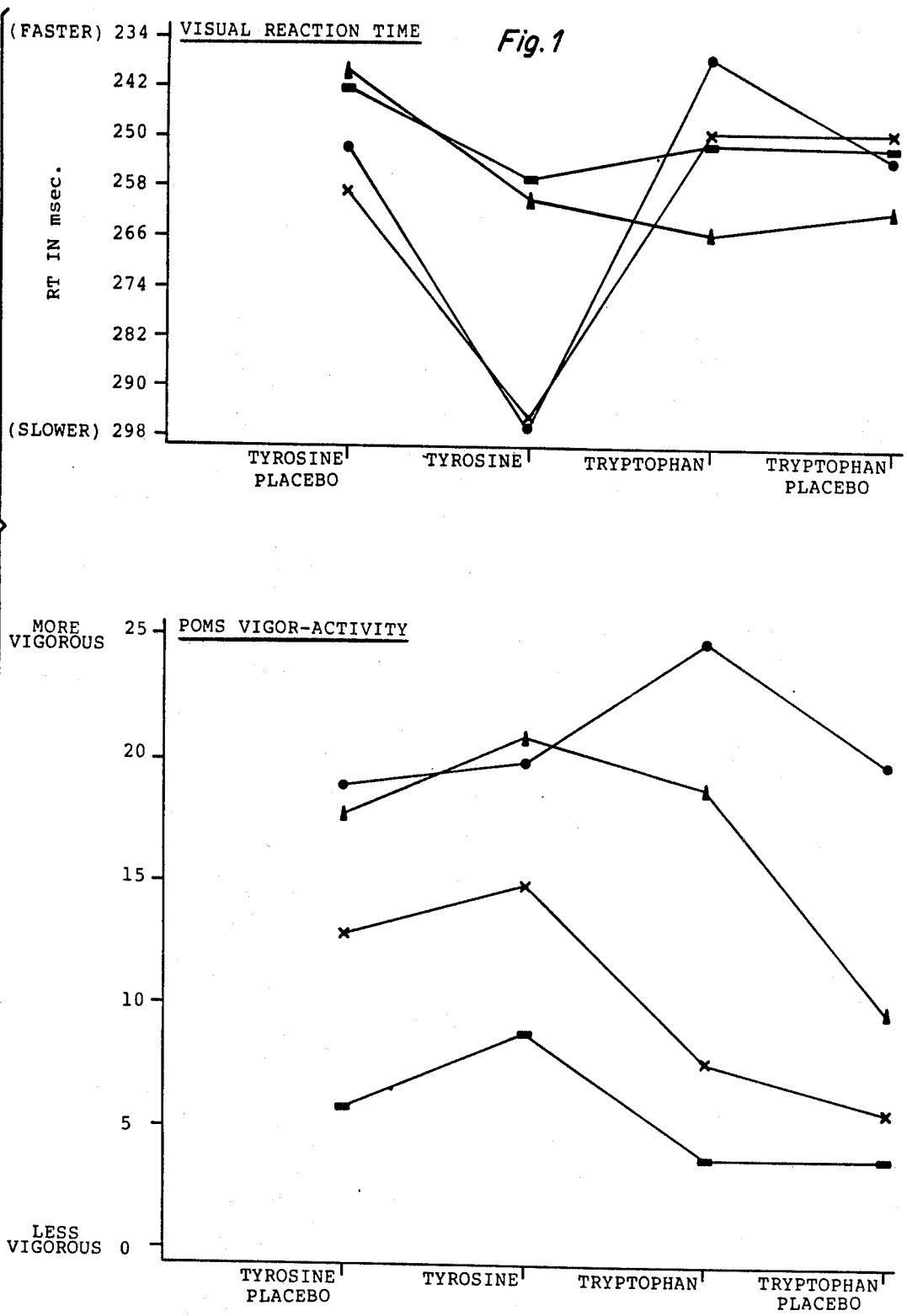
THE EFFECTS OF ORAL TYROSINE, TRYPTOPHAN, AND PLACEBO ON SELF-REPORTED VIGOR-ACTIVITY (PROFILE OF MOOD STATES). EACH LINE REPRESENTS A DIFFERENT SUBJECT. SUBSTANCES WERE INGESTED IN BALANCED SEQUENCE AT 8:30 or 9:30 A.M. DOSAGES WERE: TRYPTOPHAN (50 mg./kg.), TYROSINE (100 mg./kg.), PLACEBO (VALINE, 1g.).

PROCESS FOR IMPROVING VIGOR AND MOOD IN NORMAL HUMAN PATIENTS

BACKGROUND OF THE INVENTION

The Government has rights in this invention pursuant to Grant No. AM-14228 awarded by the National Institute of Health.

REFERENCE TO RELATED APPLICATIONS

This application is a continuation application of application Ser. No. 169,001, filed July 15, 1980, now abandoned which is a continuation of Ser. No. 066,158, filed Aug. 13, 1979, now abandoned, which is a continuation-in-part of Ser. No. 898,740, filed Apr. 24, 1978, now abandoned.

This invention relates to a method and composition for improving vigor in humans increasing the level of a catecholamine (norepinephrine, epinephrine, dopamine) in neuronal synapses.

It is well known that the neurotransmitters dopamine, norepinephrine and epinephrine are derived from dihydroxyphenylalanine (DOPA). DOPA is, in turn, produced in neurons by the enzymatic hydroxylation of the amino acid tyrosine. This process is catalyzed by the enzyme tyrosine hydroxylase. The DOPA in decarboxylated to dopamine by the enzyme aromatic L-amino acid decarboxylase (AAAD) and norepinephrine is produced from dopamine in neurons that also contain the enzyme dopamine beta-hydroxylase. It is also known that within this reaction chain, the rate-limiting step is the conversion of tyrosine to DOPA. For this reason, DOPA has been administered to patients who suffer medical disability resulting from dopamine deficiency in diseases such as Parkinson's Disease. Unfortunately, DOPA, when administered is taken up by cells throughout the body and converted to dopamine and this interferes with the normal metabolic processes in these other cells. In addition, DOPA interferes with the body's normal storage of the neurotransmitter serotonin, and lowers brain levels of the compound S-adenosylmethionine. It is believed that these effects contribute to such unwanted side-effects as the "On-Off Phenomenon" and, in some patients, psychotic symptoms. Other types of drugs that act by increasing dopamine, norepinephrine and epinephrine levels in synapses include the Monoamine Oxidase Inhibitors (which slow the destruction of these neurotransmitters) and the tricyclic antidepressants; these compounds, which are used in treating diseases like depression, also are relatively non-specific, producing many chemical effects besides increasing synaptic catecholamine levels and thus have a range of unwanted side-effects such as the dangerous increases in blood pressure that occur when people receiving monoamine oxidase inhibitors eat certain foods.

Prior attempts to increase or decrease the catecholamine levels by modifying neuronal tyrosine levels have been deemed unsuccessful because the total amounts of these compounds in brains and tissues were not noted to change. It was first observed in Wurtman et al (Science 185:183-184, July 12, 1974) that increases in brain DOPA concentrations, which, under the conditions of the experiments varied in proportion to the rates at which catecholamines were being synthesized, could be obtained by increasing brain tyrosine concentrations, and that decreases in brain DOPA concentrations could be produced by giving rats treatments that decreased brain tyrosine. An example of a treatment that increased brain tyrosine was the administration of tyrosine itself. An example of a treatment that decreased brain tyrosine was the administration of one of the other neutral amino acids, e.g., leucine, that competes with plasma tyrosine for uptake into the brain. Prior to that disclosure, it had been believed that the rate-limiting enzyme, tyrosine hydroxylase, was so saturated with tyrosine, that increases or decreases in brain tyrosine levels would not affect tyrosine's conversion to DOPA. In neither the above Wurtman et al article nor a subsequent paper by Gibson and Wurtman (Biochem. Pharmacology, 26:1137-1142, June 1977) was it actually shown that such changes in DOPA accumulation were accompanied by changes in brain dopamine, norepinephrine or epinephrine levels. Furthermore, in neither was it shown that changing brain tyrosine levels had any effect on the amounts of catecholamines released into synapses.

As disclosed in my prior filed applications, Ser. Nos. 066,158 and 898,740, depression in a human patient can be alleviated by administering to the patient tyrosine, phenylalanine or mixtures thereof. In order to regulate blood plasma levels of tyrosine or phenylalanine and thereby to form corresponding amounts of catecholamines released in synapses in the brain. Human patients afflicted with depression repeatedly are afflicted with the following characteristics: feelings of sadness, diminshed activity, early morning insomnia, inability to take pleasure in outside activity and subjective feeling of lethargy or reduced vigor. On the other hand, normal patients generally are afflicted with one or more of these characteristics only occasionally and not repetitively. It would be desirable to provide a means for treating normal patients having occasional reduced vigor, in order to provide relief from such a temporary condition. It would be desirable to provide such a means which is biochemically specific and lacks the undesirable side-effects or side-effects associated with administration of presently available drugs which have the effect of increasing catecholamine levels released in synapses in the brain. Alternatively, such a means could be used in combination with presently available drugs to treat lack of vigor, thereby to amplify their therapeutic effects.

SUMMARY OF THE INVENTION

The present invention provides a method for treating lack of vigor in human patients associated with a deficiency of catecholamines in synapses. This invention is based upon the discovery that treatments that increase neuronal tyrosine levels can also cause corresponding increases in the amounts of catecholamines released into synapses. The tyrosine, and its precursor, phenylalanine, can be administered alone or in admixture, with other neutral amino acids with or without drugs, in order to raise brain tyrosine (and phenylalanine) levels, and thereby to improve vigor, the lack of which is associated with deficiency of catecholamines in synapses. By varying the proportion of tryptophan, another amino acid, in the mixture, the synthesis and synaptic release of serotonin, another brain neurotransmitter, can similarly be controlled. Increased synaptic catecholamine levels are obtained by giving tyrosine regardless of whether the catecholamine-releasing neurons are or are not especially active. Phenylalanine can, in low doses, be used in place of tyrosine. Tryptophan's proportion in the neutral amino acid mixture can be used to regulate serotonin's release into synapses while increasing catecholamine release as described herein.

DETAILED DESCRIPTION OF SPECIFIC EMBODIMENTS

In accordance with this invention, tyrosine and/or phenylalanine and/or other neutral amino acids is administered to a patient either alone or in combination with one or more drugs thereby to increase the level of catecholamines like norepinephrine which are released into synapses. Serotonin release also can be controlled at the same time by varying the proportion of tryptophan present in the amino acid mixture. Release of a catecholamine or serotonin into synapses can be increased using amino acid mixtures whether or not the catecholine-releasing or serotonin-releasing neurons are especially active.

The composition of the amino acid mixture that is utilized depends upon the nature of the illness in the patient that is to be treated. When there is need to increase catecholamine release to increase vigor without increasing that of serotonin, tyrosin (and/or phenylalanine) is administered, with or without other amino acids not including serotonin's precursor, tryptophan, in doses ranging between 5 mg/kg and 200 mg/kg. This therapy is useful in normal human patients not afflicted with a particular disease or afflication, but who desire to increase their vigor. In some situations, phenylalanine can be used as a substitute for tyrosine, inasmuch as much of this amino acid is converted to tyrosine in the liver and released into the blood stream for uptake into the brain. However, plasma phenylalanine levels should be less than about double those of tyrosine, since at the higher levels, phenylalanine competes with tyrosine for uptake into the brain and can inhibit the enzyme tyrosine hydroxylase.

In some instances, it may be desirable to also increase brain serotonin levels while increasing catecholamine release since it appears that increasing brain serotonin levels tends to reduce depression. In these instances, the compositions administered also contain tryptophan in addition to tyrosine and/or phenylalanine and other neutral amino acids. Other neutral amino acids that these compositions can contain include the branched-chain amino acids (leucine, isoleucine, valine) as well as methionine, threonine and histidine. The amino acids can be supplied as monomers or as natural or synthetic polymers, e.g., peptides. The pheylalanine, tryptophan and tyrosine will be referred to collectively as "the useful amino acids".

The ratios of the plasma concentrations of tyrosine, phenylalanine and tryptophan to the sum of the other neutral amino acids are normally about 0.08–0.12, 0.07–0.12 and 0.06–0.14, respectively, depending on the composition of the diet. In some diseases, e.g., cirrhosis of the liver leading to coma; diabetes; hyperinsulinism; such catabolic states as starvation, cachexia, disseminated cancer, or severe burns or traumas, these ratios are abnormal, causing changes in brain dopamine, norepinephrine, epinephrine and serotonin release. The particular compositions used in these situations are designed to restore the plasma ratios to normal. To improve vigor, the goal of amino acid therapy is to raise or lower these ratios above or below their normal ranges, in order to increase the release of a catecholamine, with or without serotonin increase into synapses.

The tyrosine, phenylalanine and other neutral amino acids can be administered as free amino acids, esters, salts, natural or synthetic polymers or as constituents of foods. The route of administration can be oral or parenteral, e.g., intravenous.

The following example illustrates the present invention and is not intended to limit the same.

EXAMPLE I

A. Tyrosine/Tryptophan/Placebo—Within Subjects

In the first paradigm, hereafter referred to as the Tyrosine/Tryptophan protocol, four subjects were tested in a within subjects design over four test sessions. On each test day subjects ingested a packet containing either tryptophan (50 mg/kg body weight), tyrosine (100 mg/kg), a placebo identical in appearance to tryptophan, or a placebo identical in appearance to tyrosine. Both placebos consisted of 1 gram of the amino acid valine. Each subject took the substances in a different sequence, in a triple blind design in which neither subject, nor tester, nor data scorer knew what substance had been ingested, and scorer was blind to the subject's overt behavior during the test session.

Subjects were normal male college students examined by a physician prior to study entry. On each test morning, one subject ingested the experimental agent at 8:30 and began a 1-hour test session at 9:15. Another took the substance at 9:30 and began testing for Profile of Mood States (POMS) at 10:15. The POMS is a self-report mood questionnaire yielding factor analytically derived scales for Tension-Anxiety, Depression-Dejection, Anger-Hostility, Vigor-Activity, Fatigue-Inertia, Confusion-Bewilderment. The test consists of 65 5-point adjective rating items, and can be completed easily in 5 minutes. It was developed by McNair, Lorr and Droppelman and is marketed by Educational and Industrial Testing Service, San Diego, Calif. All scales have internal consistency reliabilities in the range of 0.90. Test-retest reliability over a median period of 20 days ranges between 0.65–0.74. Although stability is less than would be desired for measurement of a stable personality trait, it is adequate for a more ephemeral characteristic such as mood. Indeed, higher stability might challenge the construct validity of the Scale. The Vigor-Activity subscale of the POMS showed substantial changes over dietary conditions and a considerable degree of consistency across subjects. Scores for each of the four subjects in all four dietary conditions are graphed in FIG. 1. As FIG. 1 indicates, compared to their own performance on tyrosine placebo, all subjects showed a lengthening or slowing of reaction time following ingestion of tyrosine. For two subjects, the slowing on tyrosine is similar to that observed on tryptophan or tryptophan placebo, but for two others it is much more pronounced. On the Vigor scale of the POMS, all subjects show some degree of increased vigor after tyrosine ingestion as compared to tyrosine placebo, and for three, subjective vigor on tyrosine is substantially greater than vigor following ingestion of tryptophan or tryptophan placebo.

The remaining scales of the POMS showed substantial variability, so that they are difficult to interprest without a greater number of subjects.

I claim:

1. The process for improving vigor in a human patient who lacks vigor associated with a deficiency of catecholamines in synapses which comprises administering to the patient a neutral amino acid containing tyrosine in an amount effective to regulate blood plasma levels of tyrosine to form corresponding amounts of catecholamines released in synapses in the brain.

* * * * *